(12) United States Patent
Hagstrom et al.

(10) Patent No.: US 8,162,587 B2
(45) Date of Patent: *Apr. 24, 2012

(54) METHOD AND SYSTEM FOR SUPPLYING PORTABLE GAS CYLINDERS

(75) Inventors: Bradley Hagstrom, Glen Ellyn, IL (US); Paul W. Garvey, Georgetown (CA); William J. Bryce, Willowbrook, IL (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/177,173

(22) Filed: Jul. 6, 2011

(65) Prior Publication Data

US 2011/0264606 A1 Oct. 27, 2011

Related U.S. Application Data

(63) Continuation of application No. 11/876,983, filed on Oct. 23, 2007, now Pat. No. 8,002,514.

(60) Provisional application No. 60/854,044, filed on Oct. 24, 2006.

(51) Int. Cl.
*B65B 31/00* (2006.01)
*B65B 21/02* (2006.01)
*B65D 25/56* (2006.01)

(52) U.S. Cl. ............ 414/810; 414/800; 141/1; 141/231; 206/769

(58) Field of Classification Search .............. 141/1, 231; 414/800, 808, 810; 206/769
See application file for complete search history.

(56) References Cited

U.S. PATENT DOCUMENTS

| 4,022,343 | A | * | 5/1977 | Richardson | 206/521 |
| 4,766,893 | A | | 8/1988 | Drews | |
| 4,788,973 | A | | 12/1988 | Kirchgeorg et al. | |
| 4,940,049 | A | | 7/1990 | Kirchgeorg et al. | |
| 5,058,758 | A | * | 10/1991 | Suddeth | 220/724 |
| 5,829,629 | A | * | 11/1998 | Usher | 220/724 |
| 5,954,099 | A | * | 9/1999 | Princiotta et al. | 141/18 |
| 6,155,258 | A | | 12/2000 | Voege | |
| 6,209,749 | B1 | * | 4/2001 | Guess | 220/724 |
| 6,327,492 | B1 | | 12/2001 | Lemelson | |

(Continued)

OTHER PUBLICATIONS

"First Aid Oxygen—Life Oxygen Softpac Portable Oxygen Complete with Cylinder and Oxygen—O-25 Variable Flow"; Feb. 5, 2008; Web Page—(http://www.firstaidandsafetyonline.com/prod_details-catid-49-id-579.asp); pp. 1 and 2.

*Primary Examiner* — Gregory Huson
*Assistant Examiner* — Nicolas A Arnett
(74) *Attorney, Agent, or Firm* — Robert J. Hampsch

(57) ABSTRACT

A method of supplying a portable medical gas system is provided. The disclosed method includes preparing a portable medical gas system, the portable medical gas system including a cylinder adapted to be filled with medical gas and a gas dispensing valve. The portable medical gas system is place in a specialized container having a configuration adapted to hold the portable medical gas system only when the cylinder of portable medical gas system is unused state or empty state. The portable medical gas system is delivered to the customer, and returned as an empty cylinder via commercial carrier. Upon receipt of the empty or spent portable medical gas system, another portable medical gas system filled with medical gas is sent to the customer. In one embodiment, the portable medical gas system includes a single-use flow control valve which ensures the cylinder is empty after its initial use.

18 Claims, 7 Drawing Sheets

U.S. PATENT DOCUMENTS

| | | | |
|---|---|---|---|
| 6,685,404 B2 * | 2/2004 | Udivich et al. | 410/42 |
| 6,715,514 B2 * | 4/2004 | Parker et al. | 141/1 |
| RE38,533 E | 6/2004 | Kirchgeorg et al. | |
| 7,167,489 B2 * | 1/2007 | Kawakami et al. | 372/19 |
| 7,237,570 B2 | 7/2007 | Gamard et al. | |
| 7,275,902 B1 * | 10/2007 | Klotz | 410/42 |
| RE40,365 E | 6/2008 | Kirchgeorg et al. | |
| 7,784,501 B2 * | 8/2010 | Gershtein et al. | 141/100 |
| 8,002,514 B2 * | 8/2011 | Hagstrom et al. | 414/810 |

* cited by examiner

US 8,162,587 B2

METHOD AND SYSTEM FOR SUPPLYING PORTABLE GAS CYLINDERS

CROSS REFERENCE TO RELATED APPLICATIONS

This application is a continuation application of U.S. patent application Ser. No. 11/876,983 filed Oct. 23, 2007 now U.S. Pat. No. 8,002,514 and which claims priority to U.S. patent application Ser. No. 60/854,044 filed Oct. 24, 2006, the disclosure of which is incorporated by reference herein.

FIELD OF THE INVENTION

The present invention generally relates to a method of supplying portable gas cylinders such as medical oxygen cylinders, and more particularly, to a method and system for supplying full portable gas cylinders to customers and accepting return of empty portable gas cylinders via commercial carrier.

BACKGROUND

Medical gas suppliers typically have a dedicated distribution channel designed to handle the portable medical gas cylinders routinely shipped to and from its customers. Given the economics of the gas cylinder product sales and infrastructure required to support the current gas cylinder distribution model, the radius of distribution is often limited to customers within about 60 miles from each distribution center. To expand the existing proprietary distribution networks and the number of distribution centers to effectively cover the entire United States and Canada to meet the medical oxygen needs of the public sector would likely be cost prohibitive.

What is needed therefore is an alternate and cost-effective distribution channel for cylinder-based, medical gas products.

SUMMARY OF THE INVENTION

In one aspect, the present invention may be characterized as a method of continuous supply of medical gas systems comprising the steps of: (i) receiving one or more portable medical gas systems from a medical gas supplier, each portable medical gas system including a portable gas cylinder filled with medical gas, a flow control valve operatively disposed on the cylinder wherein the flow control valve includes one or more settings that empty the medical gas from the portable gas cylinder; (ii) using or emptying the medical gas from at least one of the portable gas cylinders; (iii) verifying the used portable gas cylinder is empty and packing the empty portable gas cylinder in a container configured to hold the portable gas cylinder; and (iv) return shipping the container having an empty portable gas cylinder disposed therein via commercial carrier.

In another aspect, the present invention may be characterized as a method of supplying medical gas to customers comprising the steps of: (i) delivering a portable medical gas system to a customer, the portable medical gas system including a cylinder filled with medical gas, and a flow control valve operatively disposed on the cylinder wherein the flow control valve includes a setting adapted to empty the medical gas from the cylinder; (ii) receiving notification from the customer that the portable medical gas system or cylinder requires replacement; and (iii) arranging for return shipment of the empty portable gas cylinder or the portable medical gas system with the empty portable gas cylinder via commercial carrier.

In a broader sense, the invention may be characterized as a business method of supply and use of medical gas systems or equipment by a customer comprising the steps of: (i) receiving a medical gas system or medical gas equipment, the medical gas system or medical gas equipment including at least one cylinder or cartridge filled with medical gas or other consumable required for operation of the medical gas system or medical gas equipment; (ii) using the cylinder or cartridge filled with medical gas or other consumable; (iii) verifying the cylinder is empty or cartridge is spent and packing the empty cylinder or spent cartridge in a container configured to hold the empty cylinder or spent cartridge; and (iv) return shipping the container having an empty cylinder or spent cartridge disposed therein via commercial carrier.

BRIEF DESCRIPTION OF THE DRAWINGS

For a more complete understanding of the present invention and the advantages thereof, reference is made to the following detailed description taken in conjunction with the accompanying drawings in which.

DETAILED DESCRIPTION

From a delivery and distribution standpoint, a gas cylinder with less than 40 psig of oxygen is not considered a hazardous material whereas a oxygen cylinder with a pressure of 40 psig or greater must be documented, packaged, handled, and shipped as a hazardous material. Many medical gas suppliers are fully capable of handling, packaging and shipping filled gas cylinders as a properly documented hazardous material, whether by its own distribution network or via commercial carriers.

On the other hand, empty portable medical gas systems are not considered hazardous materials and can be readily shipped via commercial carrier or commercial delivery services by the customer. However, utilization of commercial delivery services would be available only if the supplier was able to assure or guarantee the carriers that the gas cylinders packaged and return shipped by customers are empty or otherwise have less than 40 psig in the cylinder.

Figure 1:
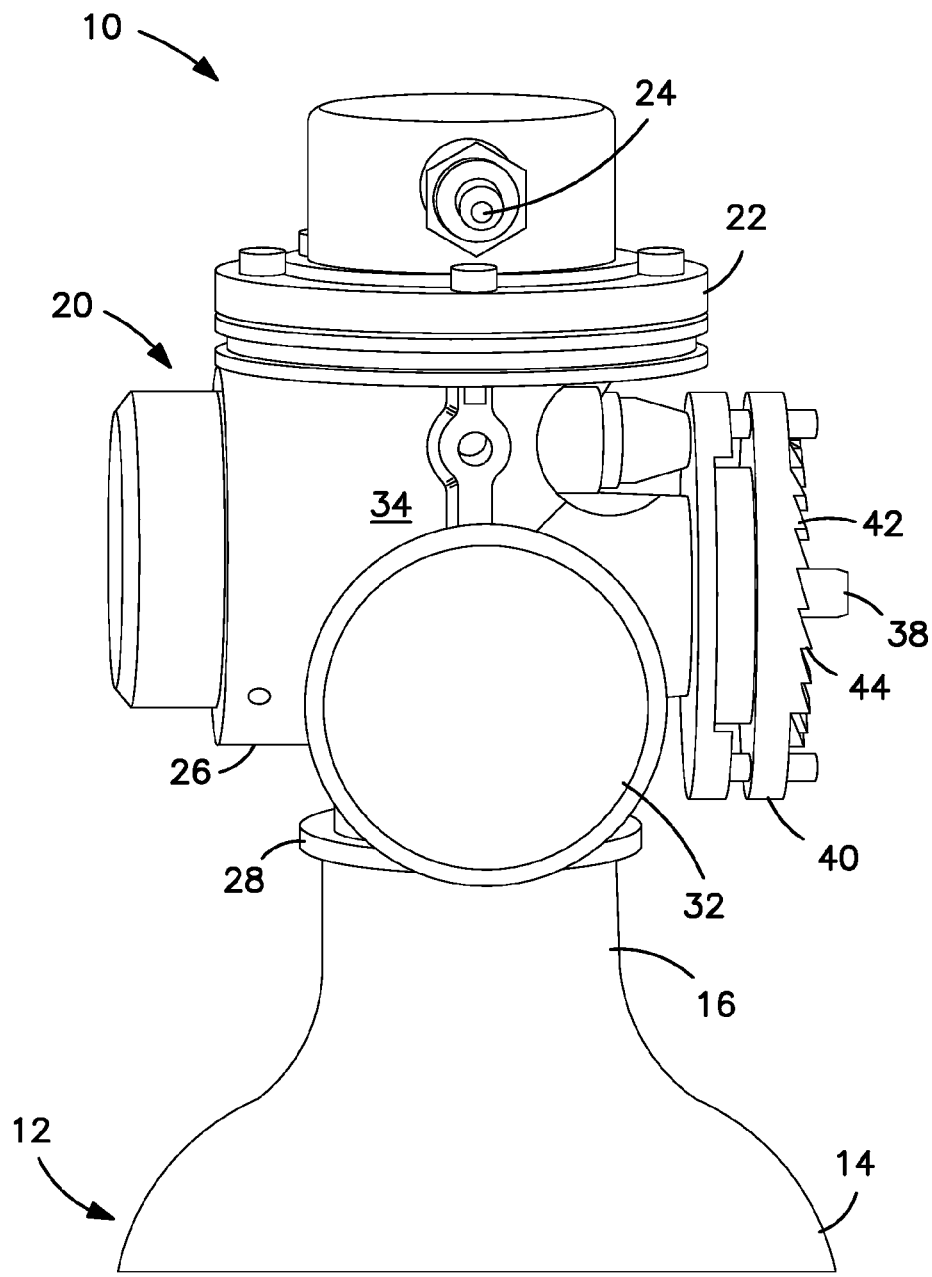
FIG. 1 illustrates a perspective view of the emergency medical gas system with a single-use flow control valve.
Figure 2:
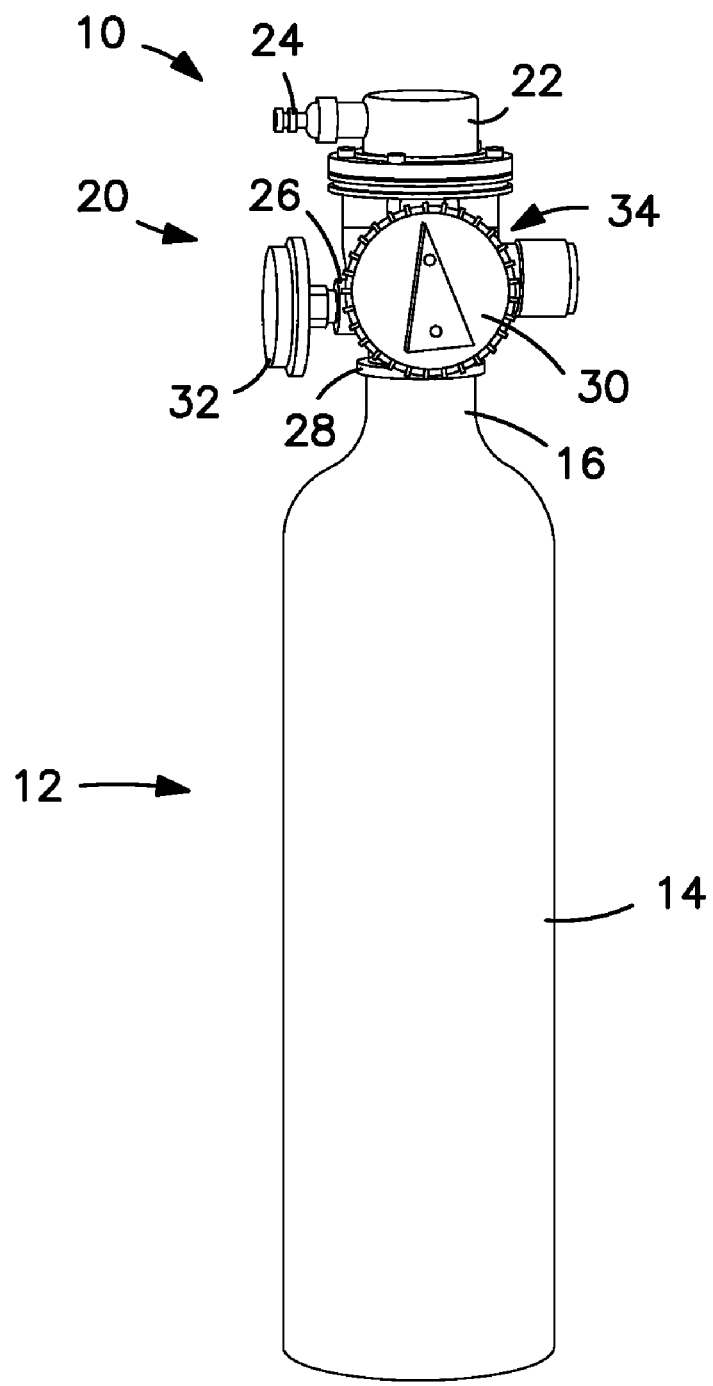
FIG. 2 illustrates another view of the emergency medical gas system with the single use flow control valve and control knob.
Figure 3:
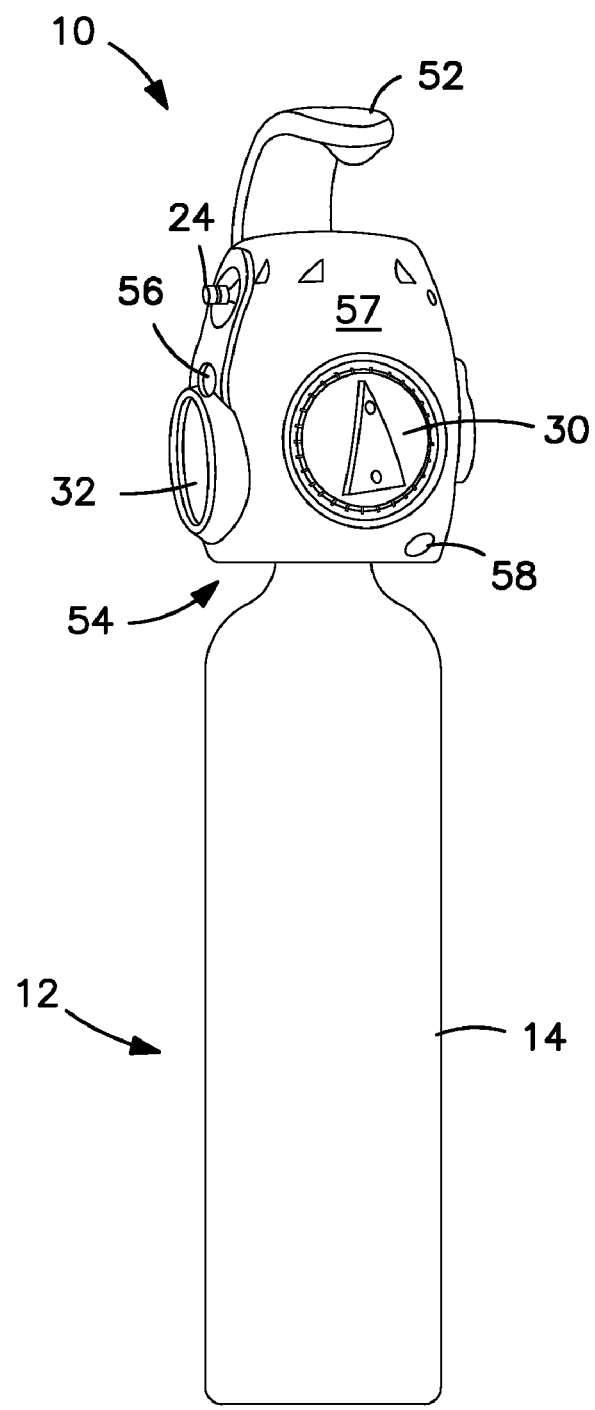
FIG. 3 illustrates a view of the emergency medical gas system with the single use flow control valve, control knob and protective shroud.

There are various means to assure that returned medical gas cylinders are empty or otherwise have a pressure of less than 40 psig in the cylinder. One preferred method, shown and described in FIGS. 1 through 3, provide a portable medical gas system that includes an integrated pressure regulator and flow control valve designed to allow the user to "open" the unit and dispense the medical gas but would prevent the user from closing the unit. Upon its initial use, the oxygen or other medical gas within the cylinder would continuously flow out of the gas cylinder until the gas cylinder reaches a sufficiently low pressure (e.g. atmospheric pressure). When empty, the pressure in the gas cylinder is below 40 psig and the cylinder can be returned as a non-hazardous material via commercial carrier. As described below, this "single-use" type flow control valve or dispensing valve is most useful for portable emergency oxygen systems and applications.

Referring now to the drawings, and in particular FIG. 1 and FIG. 2, there is shown an embodiment of the emergency medical gas system 10 for use with the present invention. The specific embodiment illustrated is designed to dispense therapeutic respiratory gas such as oxygen or mixtures of gas that might include oxygen with helium, nitrogen, carbon dioxide, nitrous oxide, nitric oxide, etc. Thus, the specific embodiment is not to be taken as limiting in that the present invention is equally applicable to other gas dispensing applications that require the use of compressed gas cylinders and the dispensing of the gas at a regulated pressure.

The emergency medical gas system 10 includes a gas cylinder 12 having a body portion 14 and a neck portion 16. Attached to the neck portion 16 of the cylinder is the gas cylinder flow control valve 20. Gas cylinder flow control valve 20 is conventionally fabricated from forged brass whereas control knob 30 is preferably fabricated from impact resistant plastic. The gas cylinder is preferably a small 3¼ inch diameter aluminum cylinder that can dispense approximately 160 liters of oxygen at 50 psig. The entire portable medical gas system is about 18 inches tall, 3¼ inches in diameter and weighs approximately 3 lbs.

Gas cylinder flow control valve 20 is provided with an upper section 22 having a gas outlet 24 to discharge the gas to be dispensed. As illustrated, gas outlet 24 is in the form of a nipple-like fitting designed to couple with a hose for dispensing the oxygen to a patient for therapeutic purposes. The gas cylinder flow control valve 20 also includes a lower section 26 that is configured to couple with the neck portion 16 of a compressed gas cylinder 12 by way of threads (not shown).

The flow rate of the medical gas from the gas cylinder is controlled by the single-use gas cylinder flow control valve 20, which is activated by control knob 30. Control knob 30 is connected to a control shaft 38 that is operatively engaged with the gas cylinder flow control valve 20. Rotation of control knob 30 in a first direction initiates the flow of the medical gas a specified flow rate by turning control shaft 38 which opens the internal flow path within the gas cylinder flow control valve 20. Once the gas cylinder flow control valve 20 is activated, high pressure gas from the gas cylinder 12 passes through an internal flow path having passages within lower section 26 and upper section 22 to the gas outlet 24. The compressed gas enters such internal flow path through a gas inlet 28 provided in lower section 26 of and is discharged after having been regulated through gas outlet 24. The actual means for pressure regulation of the medical gas is a conventional pressure regulator 34 that is designed to reduce the gas pressure to a level suitable for patient use, for instance, 50 psig. The pressure regulator 34 can also be said to divide the internal flow path for the gas into high and low pressure sides. A gauge 32 is also provided along the internal flow path on the high pressure side to measure the pressure of the medical gas and determine whether the compressed gas cylinder 12 is full, partially full or empty.

The illustrated gas cylinder flow control valve 20 is a 'single-use' valve. That is to say, once activated or opened by rotating the control knob 30 in a first direction, the pressurized gas continuously flows from the gas cylinder 12 through the gas cylinder flow control valve 20 to the outlet 24 until the gas cylinder 12 is empty. The gas cylinder flow control valve 20 cannot be closed by the user and the control knob 30 cannot be rotated in an opposite direction by the user.

In the illustrated embodiments, rotation of control knob 30 and thus the control shaft 38 is controlled by a lock collar 40 attached to flow control valve 20 proximate the control shaft 38 and corresponding projections (not shown) disposed on the underside of the control knob 30 that are aligned with the lock collar 40. Rotation of the control knob 30 in the first direction moves the projections on the underside of the control knob 30 on the rotational path along various ramp surfaces 42 on the lock collar 40. However, rotation of the control knob 30 in the opposite direction (clockwise) is prevented by a plurality of retaining abutments or surfaces 44 that engage the projections on the underside of the control knob 30 and prevent the control knob 30 from being rotated in that opposite direction and thus prevents control shaft 38 from closing the gas cylinder flow control valve 20.

The embodiment of the portable medical gas system shown in FIG. 3, has a protective shroud 50 disposed over the gas cylinder flow control valve 20. The protective shroud 50 includes various handles for carrying or manipulating portable gas cylinders 12 and gas cylinder flow control valves 20 for the administration of medical oxygen. The shroud 50 provides improved safety and versatility to the handling process of such cylinders and valves. The shroud 50 includes upper handle 52 and lower handle 54. Upper handle 52 can be formed in an inverted J-like configuration and provides a method for easily lifting the gas cylinder 12, the gas cylinder flow control valve 20, and shroud 50. Lower handle 54 is formed within the bottom portion of the composite body 56 of the shroud 50. As shown in FIG. 3, lower handle 54 includes lip portion 58 to allow the user to manipulate the shroud 50, flow control valve 20 and gas cylinder 12 by grabbing the shroud 50 in an underhand fashion or by placing one or more fingers under the lip portion 58 near the lower portion 26 of the flow control valve 20. In this manner, the portable medical gas system comprising the shroud 50, flow control valve 20, and gas cylinder 12 can be manipulated by using upper handle 52, the lower handle 54 or both the upper handle 52 and lower handle 54.

The shroud 50 is preferably configured to be part of the portable medical gas system and used in combination with a gas cylinder 12 and a gas cylinder flow control valve 20. The shroud 50 may initially be formed in a plurality of component plastic parts, which are assembled or joined together around the flow control valve 20 on top of the gas cylinder 12. The various components of the shroud 50 are preferably held together with a plurality of screws or other means for fixedly attaching the component plastic parts. In the illustrated embodiment, the shroud 50 may be formed of plastic, for example a LEXAN® plastic such as EXL1414 plastic commercially available from General Electric.

The shroud 50 is a custom fitted structure that includes a plurality of ports on the outside surface 57 of the shroud body 56 to accommodate the control knob 30, the gas outlet 24, and the gauge 32 which are either exposed via the ports or protrude through the shroud body 56 via the ports.

Figure 4:
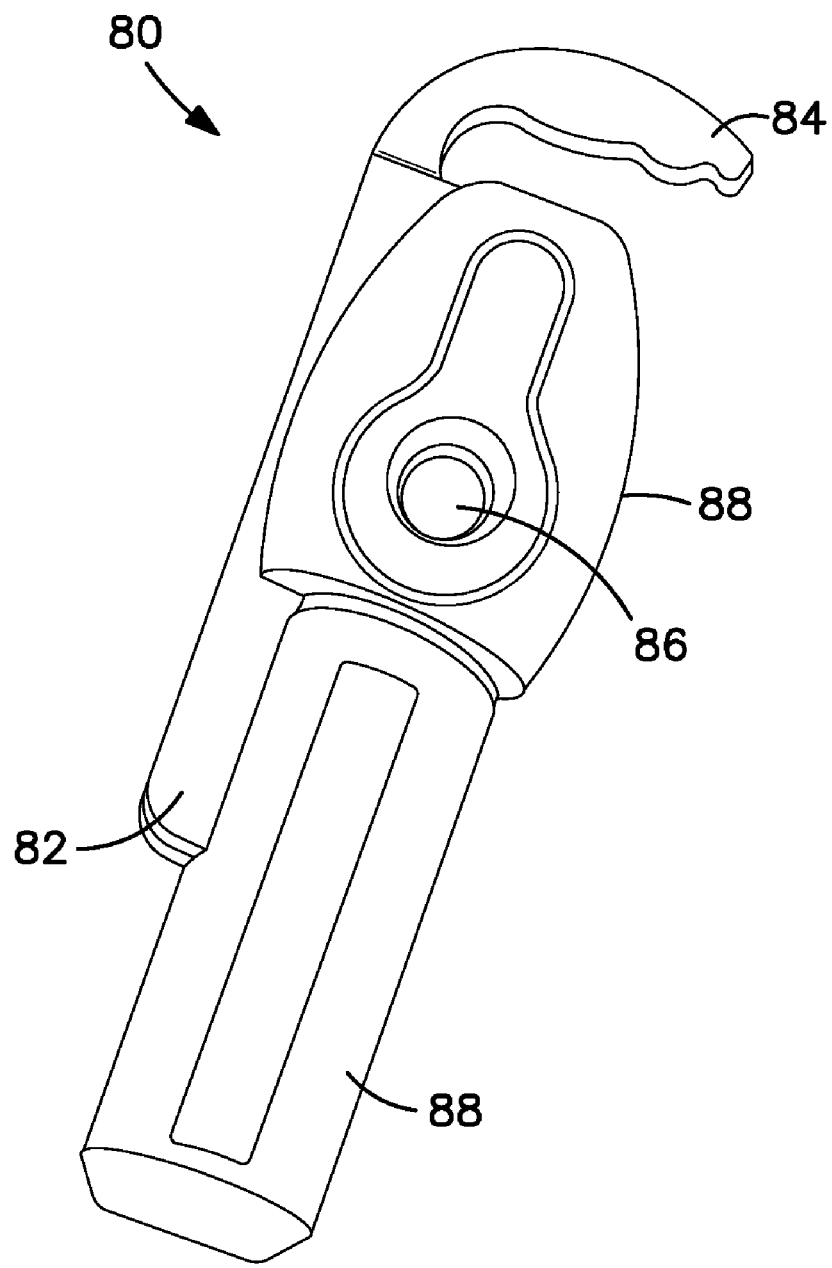
FIG. 4 illustrates a view of the portable medical gas system shipping container for use with the present emergency medical gas cylinder.
Figure 5:
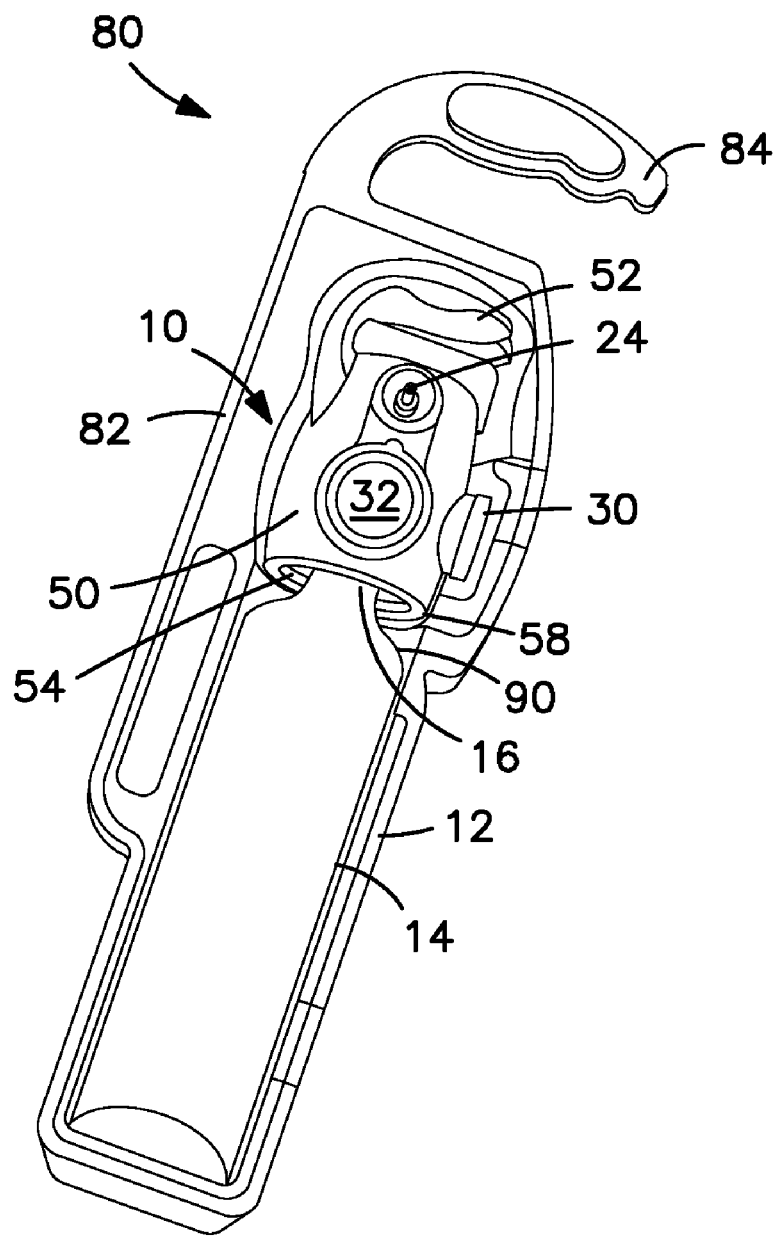
FIG. 5 illustrates another view of the portable medical gas system shipping container and an empty medical gas cylinder disposed therein.

Turning now to FIG. 4 and FIG. 5, there is illustrated a shipping container adapted for use with the present emergency medical gas system. As seen therein, the emergency medical gas system 10 is preferably shipped in a container 80 designed specifically to carry the portable gas cylinder and associated system. The container 80 preferably includes a two-part hinged body portion 82, a handle portion 84, a transparent surface, port or window 86 and a latch mechanism 88 used for opening the container 80 and securing the container 80 closed.

The body portion 82 of the shipping container 80 includes a compartment space 90 adapted to precisely receive the portable medical gas system 10 in an unused mode or in an empty mode. In various contemplated embodiments, the configuration of the emergency medical gas system 10 when pressurized in an 'ON' position, preferably would not fit into the compartment space 90 as a result of some projection, extension or other element protruding outwardly from a portion of the portable medical gas system 10.

When the emergency medical gas system 10 is properly placed in the container 80, the transparent surface or window 86 of the container 80 is adapted to align with the pressure gauge 32 of the portable medical oxygen system 10. This alignment allows the gas supplier, distributor, customer and/ or commercial carrier to visually identify whether the gas cylinder is empty or full. This visual indication would allow the commercial carrier or other person to decide at the point of cylinder pick-up whether shipment is authorized and whether the material is a properly documented hazardous material or a non-hazardous empty gas cylinder.

Although not shown, additional oxygen tubing and mask may be separately included in the shipping container 80 or packaged separately. In an emergency situation, the customer would access an emergency kit, open the container 80, remove the portable medical gas system 10 and any mask and tubing, turn on the system or unit, couple the tubing and mask to the unit, verify flow of oxygen at the mask and apply the mask to the patient. After use, the customer would contact the gas supplier for re-supply or replacement of the empty system or unit and is provided detailed instructions on how to return the empty system or unit via commercial carrier. Upon receipt of a replacement portable medical gas system 10, the customer can replenish the emergency kit and re-pack the oxygen tubing and mask with the system for future use.

Turning now to FIGS. 6A through 6D, an alternate embodiment of the present system would include a portable medical gas system with a standard or multi-use, flow regulated, gas flow control or dispensing valve that has an auxiliary or shipment setting adapted for return shipment of the empty cylinder. In such embodiment, when the control knob and flow control valve are set to the return shipment setting or 'SHIP' position, the flow control valve would open and the medical gas within the cylinder would be released and vented to the atmosphere.

Figure 6A:
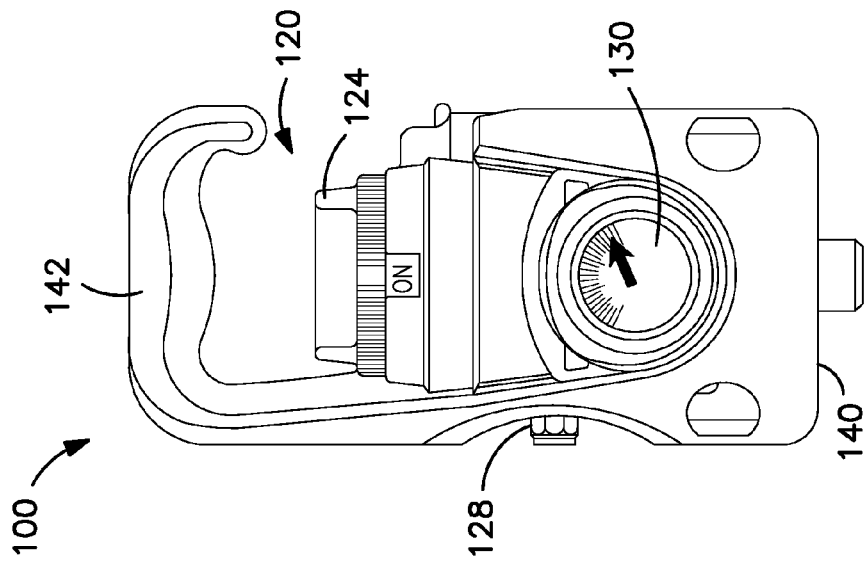
FIGS. 6A through 6D illustrate an embodiment of an emergency medical gas system with a regulated flow control valve and control knob shown in an 'OFF' position, an 'ON' position, a flow regulated '7.0' position and a 'SHIP' position, respectively.
Figure 6B:
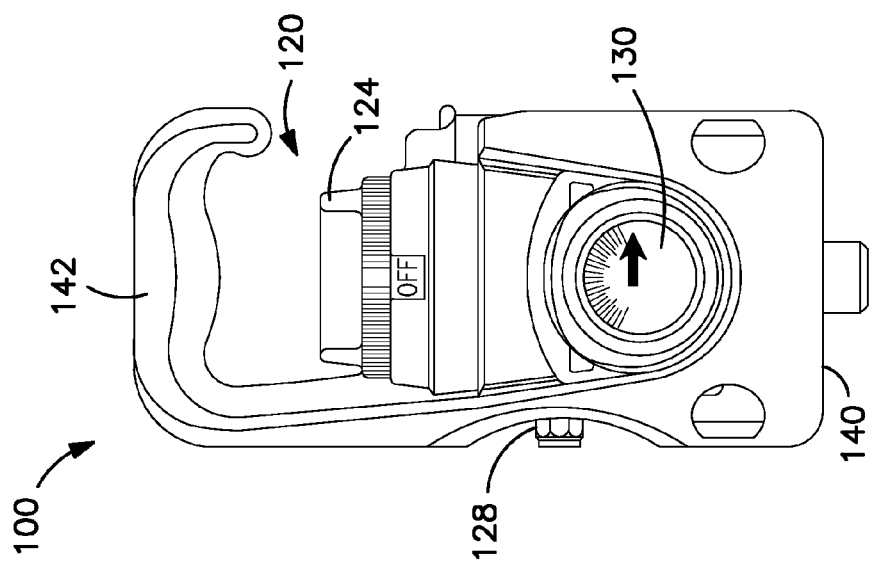
Figure 6C:
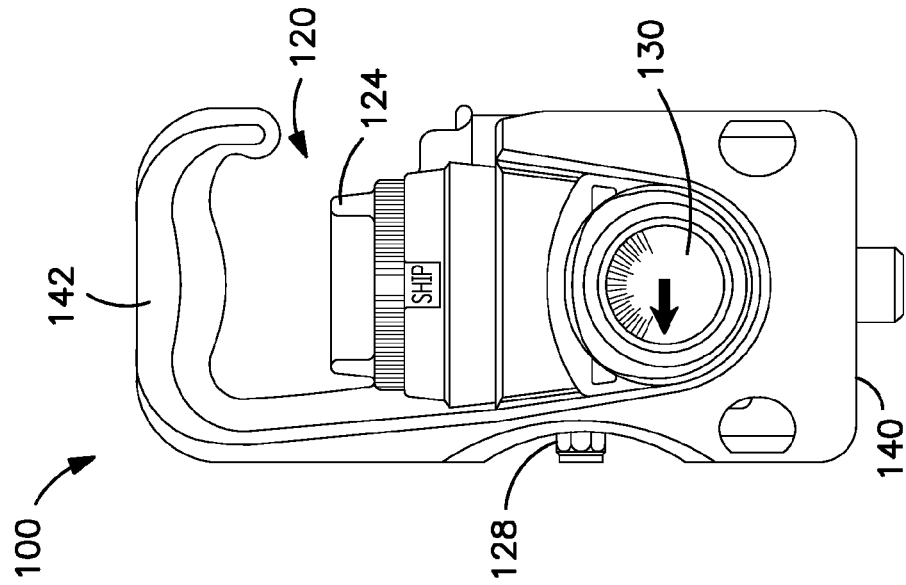
Figure 6D:
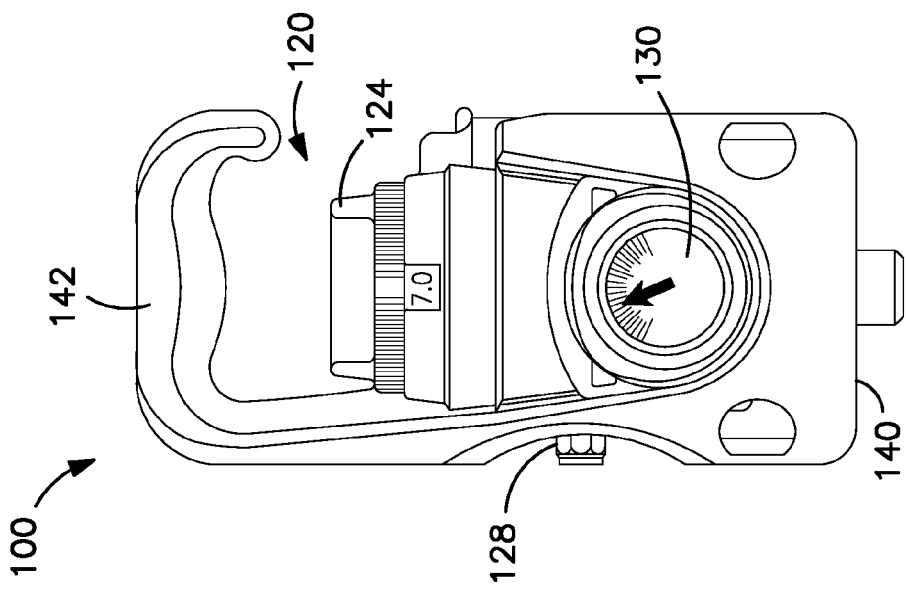

FIGS. 6A through 6D provide a partial view of an embodiment of a medical gas cylinder 100 that provides a fully regulated or fully controllable gas flow employing the 'SHIP' mode concept. As seen therein, the medical gas cylinder system 100 includes a dispensing mechanism that houses a flow control valve 120, a control knob 124 and a cylinder contents gauge 130 within a shroud 140 having an integrated handle 142. FIG. 6A depicts the control knob 124 and flow control valve 120 in an 'OFF' position where no flow of gas from the cylinder is occurring. FIG. 6B depicts the control knob 124 and flow control valve 120 in an 'ON' position where some prescribed flow of gas from the cylinder to the outlet 128 is occurring. Alternatively, as depicted in FIG. 6C, the control knob 124 and flow control valve 120 are set in a regulated flow position indicated by a numeric value (e.g. '7.0') representing the controlled gas flow from the cylinder in liters per minute. Such regulated version would likely have additional flow settings to allow a greater or less gas flow from the cylinder to the gas outlet 128 and eventually to the patient. Finally, FIG. 6D depicts the control knob 124 and flow control valve 120 in an 'SHIP' position where the flow control valve 120 is fixed in an open position and the medical gas from the cylinder is evacuated to permit shipment of the empty cylinder by commercial carrier. The shipping container used with the embodiment of FIGS. 6A through 6D would also allow for visual inspection of the position of the control knob 124 and flow control valve 120 as well as the cylinder contents gauge 130 through a window or other transparent surface.

In a 'single-use' emergency medical gas application, the embodiments shown in FIGS. 6A through 6D would allow the user to move between the 'OFF' position and an 'ON' position or regulated 'e.g. 7.0' position to initiate the gas flow, but would not allow the user to return the control knob 124 or flow control valve 120 to the 'OFF' position. Similarly, in a fully controllable medical gas application the embodiments shown in FIGS. 6A through 6D would allow the user to move the control knob 124 and flow control valve 120 between the 'OFF' position and an 'ON' position or regulated 'e.g. 7.0' position to initiate the gas flow and would also allow the user to return the control knob 124 to the 'OFF' position. When the unit is to be returned, the user would move the control knob 124 and flow control valve 120 to the 'SHIP' position to empty the gas from the cylinder. However, once in the 'SHIP' position, the control knob 124 and flow control valve 120 would be locked in that position.

As suggested above, a further contemplated embodiment of the present system alters the physical configuration of the gas cylinder to fit within the shipping container when the gas cylinder system is placed in the 'SHIP' mode. Likewise, the configuration of the medical gas system in an unused condition (as shipped by the medical gas supplier) would also fit within the shipping container. However, when the control knob or gas dispensing valve is positioned in any other regulated flow position, the configuration of the medical gas system would not fit within the shipping container and the shipping container would not close. In this manner, the customer could not inadvertently return ship a filled or highly pressurized used gas cylinder using the approved shipping container.

In this alternate embodiment, the changing shape or configuration of the emergency medical gas cylinder and system can be integrated into the control knob associated with the cylinder gas dispensing valve. Alternatively, the changing shape or configuration of the emergency medical gas cylinder and system may be a separate protruding element that is actuated upon removal of the cylinder from the container or upon initial use of the emergency medical gas system and such protruding element can only be retracted when the gas cylinder has been emptied and/or set on return ship mode. In this manner, the emergency medical gas cylinder would only fit into the shipping container when the protruding element is in the retracted position or the control knob is set to the proper position, which would assure the commercial carrier that the medical gas cylinder is empty.

It is well known that most business and households can be serviced by commercial package delivery services such as United Parcel Service (UPS) or Federal Express (FedEx). In addition, the weight and size characteristics of a typical emergency oxygen system and many of the portable medical gas systems are within the package limits set by these commercial delivery services. Thus, use of commercial carriers would be very economical and very useful if the practical and regulatory barriers to use of such commercial delivery services can be addressed.

As indicated above, when delivered as a filled, pressurized cylinder with a medical gas such as oxygen, the current portable medical gas system is still considered a hazardous material and needs to be packaged, handled and labeled as such. However, when delivered or shipped in an empty state, the empty portable medical gas system is not considered a hazardous material and can be readily shipped or transported via commercial carrier or commercial delivery services.

Using the 'single-use' flow control valve embodiment described above or the alternate embodiments described herein, the medical gas supplier would be able to assure or guarantee the commercial carriers that the used emergency medical gas systems packaged and return shipped by customers are empty or otherwise have gas at less than 40 psig in the cylinder. From a practical standpoint, this fundamentally changes the method of shipment and the overall method of distribution for medical gas cylinders. By using commercial carriers for cylinder delivery and pick-up without the risk of filled cylinders being inadvertently return shipped by customers, various distribution methods and marketing strategies are enabled.

For example, a like-for-like medical gas cylinder exchange program can be employed wherein medical gas cylinders are distributed to customers for use with instructions for return shipment of the empty cylinder. After use by the customer, the empty cylinders are return shipped via commercial carrier to a designated return location and a replacement cylinder filled with medical oxygen or other gas is subsequently returned to the customer also via commercial carrier. In addition, medical gas suppliers can also offer a pre-paid return shipment via commercial carriers for empty medical gas cylinders. Billing or charging methods may include pre-pay arrangements or automatic charging upon the occurrence of a designated event such as upon delivery of a unit, delivery of the replacement unit, receipt of the unit by a designated receiver, or even mere notification of the need for a replacement unit by the customer. Such notification, of course can occur via telephone, email or internet based communications.

The use of commercial carriers to deliver or return medical gas cylinders provides a significantly lower distribution cost when compared to the proprietary truck delivery and pick-up service presently offered by most medical gas suppliers. In addition, the constraints associated with the limited distribution radius of proprietary distribution networks, the accessibility to all customers including remotely situated customers, and inventory concerns with co-mingling of hazardous materials (i.e. filled cylinders) and non-hazardous materials (i.e. empty cylinders) can be minimized or eliminated. This results in more timely and cost effective distribution and return of portable medical gas systems.

Two intended applications of the present method of distributing medical gas cylinders include distribution and return of emergency medical oxygen as well as possible distribution of individual medical oxygen cylinders to doctors, dentists and homecare patients. The use of medical oxygen without a prescription is permitted during an emergency such as a heart attack or similar such ailment. Health research indicates a majority of patients with heart ailments would benefit from the application of supplemental oxygen during their episode. The automated external defibrillator (AED) manufactures have successfully introduced products into the public market to treat a portion of these patients and there is a perceived need to assist with the treatment of heart ailments in this market with supplemental emergency oxygen system as well. The single-use flow control valve configuration of the emergency medical gas system is ideally suited to meet this need.

Doctors, dentists and home care patients that utilize emergency medical oxygen cylinders typically require the flow of oxygen be fully metered, and shut-off when not needed or turned on again when needed. Accordingly, a multi-use gas cylinder dispensing valve configuration of the emergency medical gas system can be offered to these potential customers. Such emergency medical gas systems can be returned via commercial carrier only when the gas cylinder is empty. The commercial shipment model is equally applicable to other portable medical gas systems such as prescription based medical gas applications, such as medical oxygen home care applications. By commercially offering such medical gas cylinders to be shipped to most any customer, at any location and returned empty via commercial carriers, the new distribution model can reach many more customers and potential customers, including those customers in remote locations and in a more cost effective manner that what is available under the existing proprietary distribution systems.

While the present invention has been described with reference to several preferred embodiments, as may occur to those skilled in the art, numerous changes, additions and omissions may be made without departing from the spirit and scope of the present invention, as set forth in the claims.

What is claimed is:

1. A method of continuous supply of medical gas systems comprising the steps of:
receiving one or more portable medical gas systems from a medical gas supplier, each portable medical gas system including a portable gas cylinder filled with medical gas, a flow control valve operatively disposed on the cylinder wherein the flow control valve includes one or more settings that empty the medical gas from the portable gas cylinder;
using or emptying the medical gas from at least one of the portable gas cylinders;
verifying the used portable gas cylinder is empty and packing the empty portable gas cylinder in a container configured to hold the portable gas cylinder; and
return shipping the container having an empty portable gas cylinder disposed therein via commercial carrier.

2. The method of claim 1 further comprising the step of automatically delivering a replacement portable medical gas system including a portable gas cylinder filled with medical gas to the customer after return shipment of the empty portable gas cylinder.

3. The method of claim 2 further comprising the step of notifying the medical gas supplier that the portable medical gas system has been used or requires replacement.

4. The method of claim 1 further wherein the step of return shipping the container further comprises returning the container using a pre-paid return shipment via commercial carrier.

5. The method of claim 1 further comprising the step of receiving instructions from the medical gas supplier for return shipment of the portable medical gas system via commercial carrier, such instructions including steps to ensure the flow control valve is positioned in the setting that empties the medical gas from the portable gas cylinder.

6. The method of claim 1 further wherein each portable medical gas system includes a portable gas cylinder filled with medical gas disposed in the container suitable for return shipping via commercial carrier.

7. The method of claim 1 wherein the container comprises one or more transparent surfaces adapted to allow visual inspection of a cylinder contents gauge or the flow control valve setting when the portable gas cylinder is placed within the container.

8. The method of claim 1 wherein the flow control valve is a single-use valve wherein upon actuation of the flow control valve, the medical gas within the portable gas cylinder flows continuously until the portable gas cylinder is empty.

9. The method of claim 1 wherein the flow control valve has a setting for 'SHIP' mode wherein upon placement of the flow control valve in the 'SHIP' mode, the medical gas within the gas cylinder flows continuously from the portable gas cylinder until the portable gas cylinder is empty.

10. A method of supplying medical gas to customers comprising the steps of:
   delivering a portable medical gas system to a customer, the portable medical gas system including a cylinder filled with medical gas, and a flow control valve operatively disposed on the cylinder wherein the flow control valve includes a setting adapted to empty the medical gas from the cylinder;
   receiving notification from the customer that the portable medical gas system or cylinder requires replacement; and
   arranging for return shipment of the empty portable gas cylinder or the portable medical gas system with the empty portable gas cylinder via commercial carrier.

11. The method of claim 10 further comprising the step of delivering a replacement portable medical gas system or portable gas cylinder filled with medical gas to the customer upon notification from the customer that the portable medical gas system requires replacement or upon return shipment of the empty portable gas cylinder.

12. The method of claim 10 wherein the step of arranging return shipment of the portable medical gas cylinder system or empty portable gas cylinder via commercial carrier further comprises providing a container configured to hold the empty portable gas cylinder to the customer, said container suitable for shipment via commercial carrier and engaging a commercial carrier via pre-paid return shipment to pick-up the container with empty portable gas cylinder from the customer.

13. The method of claim 12 wherein the container suitable for return shipping via commercial carrier is provided to the customer at time of delivery and disposed in said container is the portable medical gas system including a gas cylinder filled with medical gas container.

14. The method of claim 12 wherein the container comprises one or more transparent surfaces adapted to allow visual inspection of a cylinder contents gauge or the flow control valve setting when the portable gas cylinder is placed within the container.

15. The method of claim 10 further comprising the step of providing instructions to the customer for return shipment of the portable medical gas system via commercial carrier, such instructions including steps to ensure the flow control valve is positioned in the setting that empties the medical gas from the portable gas cylinder.

16. The method of claim 10 wherein the flow control valve is a single-use valve wherein upon actuation of the flow control valve, the medical gas within the portable gas cylinder flows continuously until the portable gas cylinder is empty.

17. The method of claim 10 further comprising the step of charging the customer upon delivery of the portable medical gas system; upon delivery of the replacement portable medical gas system; or upon receipt of the portable medical gas system.

18. A business method of supply and use of medical gas systems or medical gas equipment by a customer comprising the steps of:
   receiving a medical gas system or medical gas equipment, the medical gas system or medical gas equipment including at least one cylinder or cartridge filled with medical gas or other consumable required for operation of the medical gas system or medical gas equipment;
   using the cylinder or cartridge filled with medical gas or other consumable;
   verifying the cylinder is empty or cartridge is spent and packing the empty cylinder or spent cartridge in a container configured to hold the empty cylinder or spent cartridge; and
   return shipping the container having an empty cylinder or spent cartridge disposed therein via commercial carrier.

* * * * *